United States Patent [19]

Morton et al.

[11] Patent Number: 5,439,989

[45] Date of Patent: Aug. 8, 1995

[54] EPOXY RESINS BASED ON MACROCYCLIC COMPOUNDS

[75] Inventors: Trevor C. Morton, Hampton; Jonathan H. Hodgkin, Burwood; Buu N. Dao, Lalor, all of Australia

[73] Assignee: Commonwealth Scientific & Industrial Research Organisation, Campbell, Australia

[21] Appl. No.: 30,303

[22] PCT Filed: Oct. 3, 1991

[86] PCT No.: PCT/AU91/00455

§ 371 Date: May 3, 1993

§ 102(e) Date: May 3, 1993

[87] PCT Pub. No.: WO92/06128

PCT Pub. Date: Apr. 16, 1992

[30] Foreign Application Priority Data

Oct. 3, 1990 [AU] Australia ............ PK2610/90
Dec. 12, 1990 [AU] Australia ............ PK3871/90

[51] Int. Cl.6 .......... C08G 8/12; C08G 8/28; C08G 8/32; C08G 8/36
[52] U.S. Cl. ............ 525/502; 525/507; 528/98; 528/91; 549/517; 549/559; 549/560; 428/413
[58] Field of Search .......... 525/507, 502; 528/98, 528/91; 549/517, 559, 560; 428/413

[56] References Cited

U.S. PATENT DOCUMENTS 4,259,464 3/1981 Buriks et al. ............ 525/505
5,218,060 6/1983 Rolfe et al. ............ 525/507

FOREIGN PATENT DOCUMENTS 1278139 4/1990 Germany .

OTHER PUBLICATIONS

Patent Abstracts of Japan, C-742, p. 118, JP A 2-123126, 10 May 1990.

Journal of Organic Chemistry, vol. 50, issued 1985, Washington, D.C., Gutsche et al., 5802–5806.
Journal of the American Chemical Society, vol. 103, issued 1981, Washington, D.C., Gutsche et al., 3782–3792.
Journal of Organic Chemistry, vol. 43, No. 25, issued 1978, Washington, D.C., Gutsche et al., 4905–4906.
British Journal of Pharmacology, vol. 10, issued 1955, Cornforth et al. 73–86.

*Primary Examiner*—Frederick Krass
*Attorney, Agent, or Firm*—Bacon & Thomas

[57] ABSTRACT

Macrocyclic epoxy resins comprising at least one compound of the formula (I)

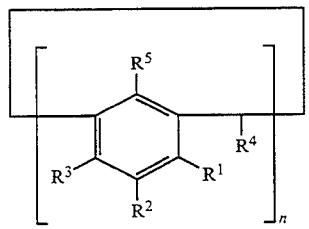

wherein
n is an integer from 3 to 10.
$R^1$ and $R^3$ are either the same or different and are selected from hydrogen, hydroxyl, alkoxy, allyloxy and epoxypropyloxy (glycidyloxy);
$R^2$ is selected from hydrogen, arylakalkyl optionally substituted with halogen, alkyl optionally substituted with halogen, and aryl optionally substituted with halogen;
$R^4$ is selected from hydrogen, alkyl optionally substituted with halogen, arylalkyl optionally substituted with alkyl or halogen, and aryl optionally substituted with halogen;
$R^5$ is selected from hydrogen, aryl and alkyl; with the proviso that the resin contains on average at least one epoxy group per molecule.

10 Claims, 2 Drawing Sheets

EPOXY RESINS BASED ON MACROCYCLIC COMPOUNDS

The invention relates to epoxy group-containing macrocyclic compounds suitable for use as epoxy resins which when formulated and cured give polymer matrices having high glass transition temperatures.

In this specification the term "epoxy resin" is used to denote a mixture of chemical compounds containing on average one or more epoxy groups per molecule. Epoxy resins are commonly reacted with curing agents (hardeners) usually in the presence of other additives such as catalysts, toughening agents, reinforcing fibres or fillers, to produce crosslinked cured resin composites which are useful for structural purposes. Such mixtures of ingredients before reaction occurs are referred to as curable epoxy resin formulations; all ingredients may be combined in one container (one-pack formulation) or the epoxy resin and curing agents may be in separate containers (two pack formulation). In the latter case the two parts Of the formulation are mixed immediately before curing.

Epoxy resins based on phenols form a significant portion of the thermosetting resins in commercial use. Of these epoxy resins, the diglycidyl ethers of bisphenol A (DGEBA) and their analogues are the most important for use in composite materials and adhesives. Other epoxy resins based on phenol/formaldehyde Novolac resins are also used and offer advantages in some applications. Existing resins of this latter type are glycidyl derivatives of linear oligomers made from various phenols and formaldehyde.

The glycidyl ether type epoxy resins known in the art, when cured, tend to have glass transition temperatures ($T_g$) which are too low for high temperature use, for example, as matrices in composite materials for use in advanced aerospace and automotive applications. A low $T_g$ of the matrix material leads to an early fall-off in mechanical properties of a laminate with rise in temperature.

Epoxy resins of a different type in which the glycidyl ether groups are replaced by N-glycidyl substituents have been developed which show limited improvement in $T_g$. These are used extensively in the advanced composites industry at the present time. However, they have the disadvantage of being based on highly toxic bisarylamines such as methylene dianiline and have different cure characteristics to the glycidyl ether-type resins which can lead to a problem of differential curing and deterioriation in mechanical properties in compositions containing both types.

The present invention provides an alternative to this latter approach which uses glycidyl ether-type epoxy resins based on more rigid macrocyclic structures built up from simple, cheap phenols of low toxicity. The cured resin formulations have better high temperature performance than those based on existing glycidyl ethers. Moreover, the formulations can also contain the diglycidyl bisphenol A type resins without significant detriment to $T_g$.

BRIEF DESCRIPTION OF THE DRAWINGS

In the following, reference will be made to the accompanying drawings, in which.

Figure 1:
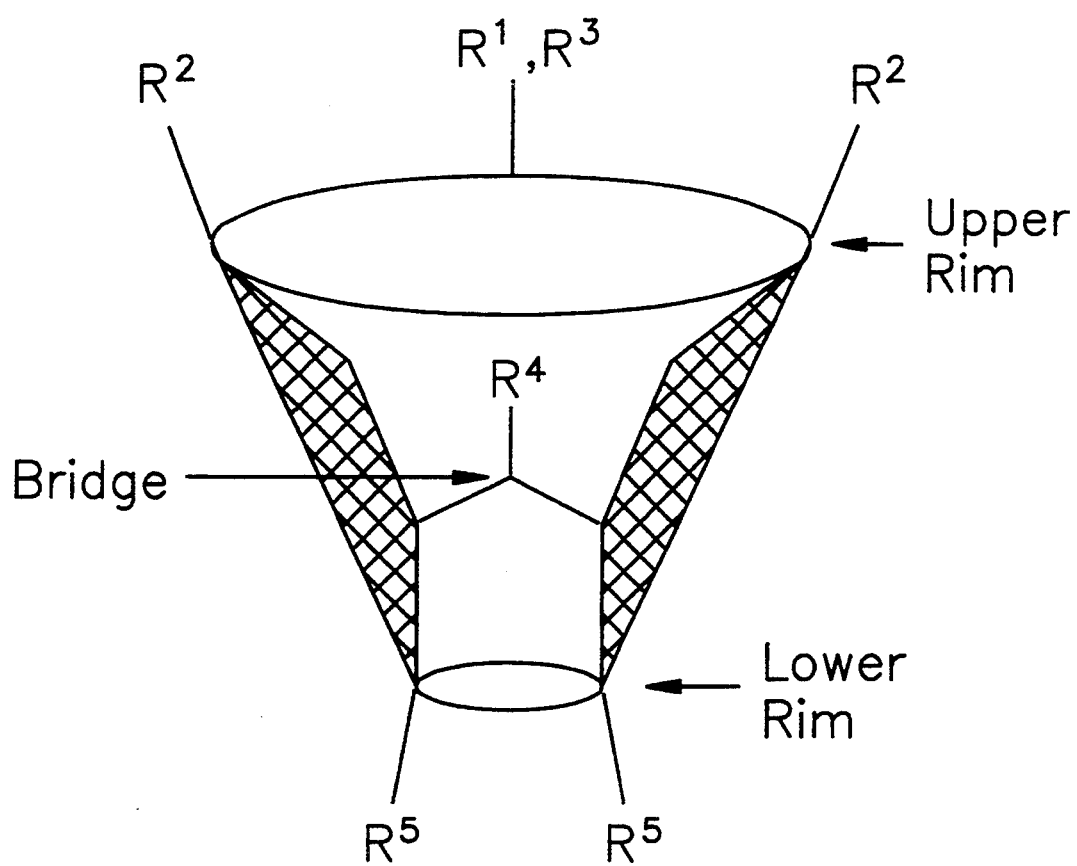
FIG. 1 is a diagrammatic representation of a calixarene.

Macrocyclic structures can be synthesized by reaction of specific phenols with aldehydes under special conditions. These are well defined chemical compounds with Zinke and Zeigler, 1944, Ber., 77, 264; Niederl and Vogel. 1940, J. Am. Chem. Soc, 62, 2512, Cornforth et al., 1955, Br. J. Pharmacol., 10, 73 making early contributions to their synthesis and structural elucidation. More recently, Gutsche (Gutsche and Muthukrishnan, 1978, J. Org. Chem., 43,4905) has assigned such compounds the collective name "Calixarenes" because they often adopt a conformation in which the aryl rings are arranged to form the sides of an urn or calix as shown in FIG. 1. It is compounds of this type that form the precursors of the resins of the present invention.

So far, calixarenes have found only limited use in polymer chemistry. A recent summary of such applications can be found in the article by Perrin and Harris (Topics in Inclusion Science, Vicens. J. and Bohmer, V., Eds., pp 235-257).

Gutsche et at., 1985, J. Org. Chem., 50,5802 refer to an epoxy derivative of a calixarene which was prepared from tetra-allyl-tetra-p-tolylsulphonylcalix[4]arene during attempts to convert this compound to the aldehyde. Oxidation with m-chloroperbenzoic acid was said to have "proceeded smoothly to yield a crystalline solid, which possesses a $^1H$ nmr spectrum commensurate with epoxide structure". The product of this reaction was implied to be a 5,11,17,23-substituted-(2,3-epoxy)propyl derivative of calix[4]arene. The authors later revealed that the product was a mixture and that "attempts to convert the epoxide to an aldehyde with $BF_3$-etherate yielded a white, cellulose-like material that was insoluble in all the usual organic solvents".

Figure 2:
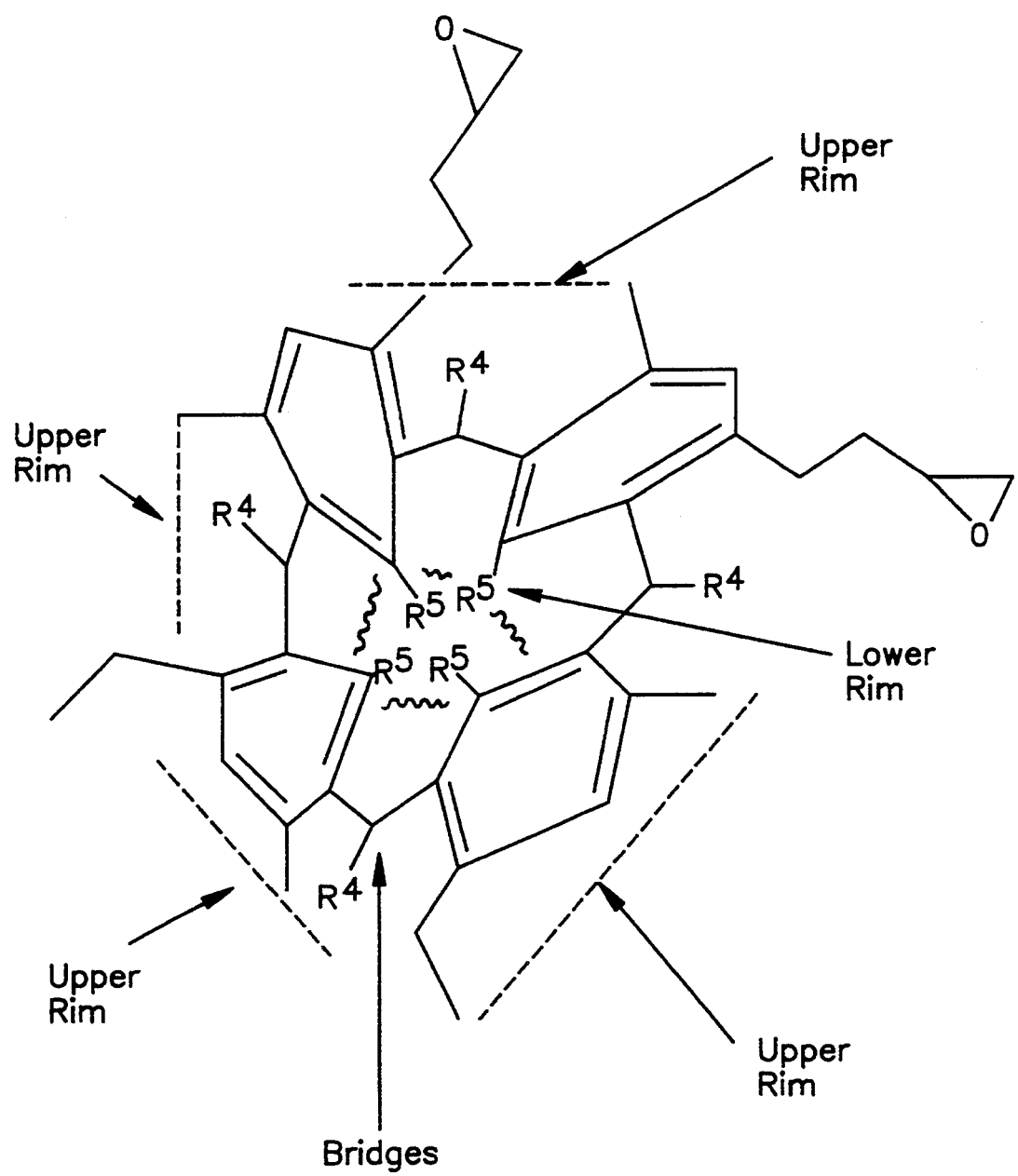
FIG. 2 is a plan view of an upper rim epoxy calixarene.

Calixarenes can be made with hydroxy substituents in either the "lower rim" or the "upper rim" (as shown in FIGS. 1 and 2). In U.S. Pat. No. 4,259,464, which related to improved synthesis of calixarenes of the type having the hydroxy groups on the lower rim, Buriks, Fauke and Munch suggest that these compounds can be reacted with various reagents such as: "Alkylene oxides, such as ethylene, propylene, butylene, styrene, etc., oxides, epihalohydrin, glycide, glycidyl ethers, epoxidized vinyl compounds, such as a-olefin epoxides etc." We have found experimentally that the lower rim hydroxy, calixarenes of the type listed in U.S. Pat. No. 4,259,464 give only the halohydrin with epihalohydrin and will not give an epoxy compound under the normal conditions of epoxidation.

More recently Goerman, Koecke, Bieroegel, Tarnow, Sierk and Raddatz ((DD 278139 A1 (Chem. Abs. 114, (15), 142900z, 2-5-91)) have disclosed a process for preparing epoxy derivatives of some calixarenes. In this process, glycidyl ethers are prepared by direct reaction with epichlorohydrin on calixarenes of the type described herein as "lower rim" calixarenes and which we have found do not give epoxy derivatives normally by direct reaction with epihalohydrins. The epoxy resins of the present invention are upper rim calixarenes. The novelty in DD 278139 A1 resides in the use of a phase transfer agent and prolonged reaction times to affect the reaction. By this process, calixarenes are said to be functionalized with groups of high reactivity for the purpose of attaching the calixarenes to polymer or biochemical materials. There is no mention of the use of these materials as resin matrix materials. The epoxy equivalent weights attained for the materials of DD 278139 A1 are too high, for example 490 g for the epoxy derivative of t-butylcalix[8]arene, to be suitable for use in composites. Furthermore, we have found that under curing conditions the epoxy derivatives of t-butyl substituted calixarenes, especially in the presence of the boron trifluoride catalysts are prone to some dealkylation leading to voidage in the resultant matrix.

We have repeated the preparation described in Example 3 of DD 278139 A1 and produced epoxy derivatized t-butylcalix[8]arene of epoxy equivalent weight 390 g. Curing of this material (Resin A) in our standard system produced an heterogeneous material of $T_g$ (Tan δ 199° C.) inferior to the resins produced in accordance with the present invention. This result is similar to that obtained on curing of an epoxy derivative of t-burylcalix-[8]arene synthesized by an indirect method in the present work and described below as Resin B.

The use of some calixarenes as hardeners with commercial epoxy resins was described in Maeda and Uchida,1990, *Netsu Kokasei Jushi,* 11, 79 and in JP 02,123,126. The advantages claimed are "thermostability, greater elasticity and a higher glass-transition temperature" in the cured resins. JP 02,123,126 states that the epoxy groups of bisphenol A type resin did not react with the hydroxyl groups of t-butylcalix[4] and [8]arene in the presence of a primary amine such as triethylenetetramine, but did react in the presence of a tertiary amine such as N,N-dimethylbenzylamine.

We have now found that improved epoxy resins can be prepared from "upper rim" calixarenes such as C-methylcalix[4,]resorcinarene(2,8,14,20-tetramethyl-4,6,10,12,16,18,22,24-octahydroxycalix-4-arene) which are synthesized from reaction of resorcinol or derivatives thereof and other phenols with various carbonyl compounds. We have found that the use of calixarenes gives better viscosity properties to the resins and that the resins when cured have considerably higher glass transition temperatures than the glycidyl ether type resins in current use.

According to one aspect of the invention there is provided a macrocyclic epoxy resin comprising at least one compound of the formula (I)

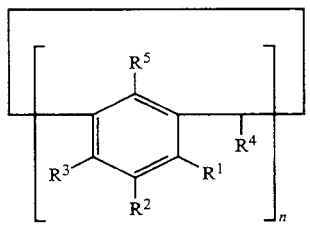

(I)

wherein n is an integer from 3 to 10;

$R^1$ and $R^3$ are either the same or different and are selected from hydrogen, hydroxyl, alkoxy, allyloxy and epoxypropyloxy (glycidyloxy);

$R^2$ is selected from hydrogen, alkyl optionally substituted with halogen, aralkyl optionally substituted with halogen, and aryl optionally substituted with halogen;

$R^4$ is selected from hydrogen, alkyl optionally substituted with halogen, aralkyl optionally substituted with halogen, and aryl optionally substituted with alkyl and/or halogen;

$R^5$ is selected from hydrogen, aryl and alkyl; with the proviso that the resin contains on average at least one epoxy group per molecule.

All alkyl moieties may be straight chain or branched. Preferably such alkyl groups contain from 1 to 20 carbon atoms.

In this specification "aralkyl" means a straight chained or branched alkyl group, substituted with one or more aryl groups, for example, benzyl, diphenyl methyl.

Substituents $R^1$, $R^2$, and $R^3$ are on the "upper rim", $R^5$ is on the "lower rim" and $R^4$ is the substituent on the "bridging group" —C(R)— of the calixarene (see FIGS. 1 and 2).

A preferred group of compounds of the formula (I) are those wherein each of $R^1$ and $R^3$ is hydroxyl, alkoxy or epoxypropyloxy, $R^2$ is hydrogen, $R^4$ is methyl, ethyl or propyl and $R^5$ is hydrogen.

A particularly preferred group of compounds of formula (I) are those in which the number of hydroxyl (or hydroxyl+alkoxy) groups is approximately equal to the number of epoxypropyloxy groups.

Epoxy resins of this invention may be prepared either directly or indirectly by epoxidation of calixarene precursors which themselves are prepared by reaction of the appropriate phenol with an aldehyde either in the presence of acid or alkali under conditions which are adjusted to give cyclic structures. The methods used for the preparation of the calixarene precursors are similar to those already described in the literature and involve addition of the aldehyde to the phenol under controlled conditions in the presence of acid or base and heating in an appropriate solvent often with provision for removal of the water of reaction. The precursors used in the present invention are those with hydroxyl groups on the "upper rim" and can be epoxidized directly with epichlorohydrin. The alternative procedure for epoxidation which involves preparing the allyl ethers could be used but these derivatives undergo rapid polymerization on treatment with peracids for the oxidation. However, it will be appreciated that other suitable known methods could be employed.

The epoxy group content and physical characteristics of the resin can be regulated by masking the hydroxy functionality prior to epoxidation by formation of ether groups such as methoxy or alkoxy or by altering the epoxidation conditions. Chemical variations are possible on the bridges of the resin, on the rim functionality and on the degree of polymerization thus allowing fine tuning of the properties.

According to another aspect of the present invention there is provided a method for the preparation of a macrocyclic compound of the formula (I) as defined above, characterized in that said method comprises epoxidizing a compound of the formula

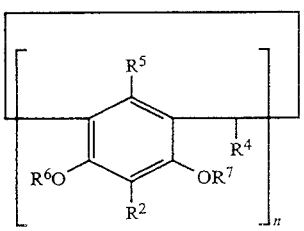

(II)

wherein n, $R^2$, $R^5$ and $R^4$ are as defined for the compound of formula (I) and $R^6$ and $R^7$ are either the same or different and are selected from hydrogen or a masking group, with the proviso that at least one of $R^6$ and $R^7$ is hydrogen.

Epoxidation may be performed using epichlorohydrin or any other suitable reagent.

According to a further aspect of the present invention there is provided an epoxy resin formulation, characterized in that the formulation comprises an epoxy resin consisting of macrocyclic compounds of the formula (I) as defined above.

According to a still further aspect of the present invention there is provided a curable epoxy resin formulation, characterized in that the resin comprises an epoxy resin as defined above, together with one or more other epoxy resins and/or additives such as are known per se in the art, e.g. toughening polymers,: hardeners and catalysts.

The epoxy resins prepared generally have epoxy equivalent weights ranging from 170 to 400 and are low melting point solids. In a curable formulation they may be used as the sole epoxy resin or in admixture with another epoxy resin, such as, for example, commercial DGEBA which has the advantage of being a glycidyl ether also. They may be used in combination with an amine hardener. such as, for example, the amine DDS and cured at temperatures up to 250° C. Other hardeners such as anhydrides may also be used. The curing reaction may be catalysed by addition of, for example, $BF_3$-ethylamine, $BF_3$-benzylamine or other known catalysts. The toughening polymers may be either elastomers or thermoplastics.

The curing may be carried out using any suitable known technique such as, for example, in an autoclave, hot platten press or other device.

Compounds of the formula (I) as stated above wherein $R^5$ is hydroxyl, allyloxy or epoxypropyloxy group are discussed hereinafter for purposes of comparison. Particularly preferred epoxy resins are listed in Table 1 below.

TABLE 1

Structures of some resins according to this invention

| Resin of Example Number | $R^1$ | $R^2$ | $R^3$ | $R^4$ | $R^5$ | n |
|---|---|---|---|---|---|---|
| 1. | OGly | H | OH | Me | H | 4 |
| 2. | OGly | H | OH | Et | H | 4 |
| 3. | OGly | H | OH | i-Pr | H | 4 |
| 4. | OGly | H | OH | Ph | H | 4 |
| 5. | OGly | H | OMe | Me | H | 4 |
| 6. | OGly | H | OH | n-Pr | H | 4 |
| 7. | OGly | Me | OH | Me | H | 4 |
| 8. | OGly | H | OH | Me | H | 4 |
| For Comparison Purposes | | | | | | |
| Resin A | H | t-Bu | H | H | OGly, OH | 8 |
| Resin B | H | t-Bu | H | H | OGly, Allyl | 8 |

Where OGly = $OCH_2CH(O)CH_2$

Notes: These are "idealized" structures. In a given resin preparation there is a number of regioisomers present involving inter-change in position of groups at $R^1$ and $R^3$. Also some masking of hydroxyl groups, giving rise to alkoxy groups, may occur during epoxidation.

By way of example, resin formulations according to the present invention, which also contain the resin DGEBA, a diarylamine hardener and a catalyst when cured by heating in stages to 180° C. with or without post-cure (heating unrestrained in air) have glass transition temperatures above 200° C. and usually in the range 270°–300° C. as shown in Table 3 (below). $T_g$ values in this latter range are preferred for the applications envisaged for the resins of the invention. For comparison, glycidyl ether type epoxy resins of the prior art have $T_g$ values up to 240° C.

Fracture toughness values ($K_q$) of the cured resin formulations containing only epoxy resins and hardeners are in the range 0.4 to 0.6 MPa. $m^{\frac{1}{2}}$. Greater toughness can be obtained by formulation of the resins with a variety of toughening agents such as various rubbers and thermoplastic materials; such formulations typically give toughness values from 0.5 to 0.8 MPa.$m^{\frac{1}{2}}$.

The epoxy resins of the present invention are particularly useful in the manufacture of fibre-reinforced composite materials.

For example, the resin formulations of the invention may be applied to reinforcing cloth such as uni-directional or woven carbon fibre either from solution (preferably a lower aliphatic ketone or halogenated hydrocarbon solvent) or from a hot melt. Application may be manual or by a machine process including those involving transfer from a precoated transfer medium.

In another aspect, the present invention provides an impregnated fibre reinforced material (commonly known as a "prepreg"), characterized in that the fibre reinforcements are impregnated with an epoxy resin formulation defined above.

The impregnated fibre materials can be laid down by any suitable known method for making composite materials such as, for example, vacuum bagging on a caul plate or on an appropriate tool.

The impregnated fibre reinforced materials are suitable for use in the production of advanced composite materials.

Thus, in a further aspect, the present invention provides an advanced composite material comprising a fibrous material in a matrix of a cured epoxy resin formulation in accordance with the invention defined above.

Alternatively, the resins of the invention can be used in an appropriate formulation for resin transfer moulding or for manufacture of sheet moulded material. Another envisaged application is in pultrusion.

The invention is further described by the following non-limiting examples.

COMPARATIVE EXAMPLES

The preparation of a "lower rim" calixarene epoxy resin (Resin B) by the indirect method is described in Example A and a further "lower rim" calixarene epoxy resin (Resin A) was made by the method described in DD 278139A1. These examples are included for comparison and illustrate the much greater ease of preparation and better properties of the "upper rim" calixarene epoxy resins of this invention.

Example A—Epoxy resin from
Octa-t-butyl-octahydroxycalix[8]axene(p-t-butylcalix-[8]arene) (Resin B)

The method used to make p-t-butylcalix[8]arene starting material was based on that of Gutsthe et a.1, 1981, *J. Am. Chem. Soc,* 103, 3782. An epoxy. resin is difficult to synthesize by direct reaction with epichlorohydrin on this type of "lower rim" calixarene (see FIG. 1 ) and yields only the chlorohydrin derivative using the procedures described above. Thus the ether: Octa-t-butyl-octaalloxycalix[8]arene was prepared first.

The p-t-butylcalix[8]arene (1.07 g, 0.00083 mole) was dissolved in dry. DMF (25 ml) and placed in an apparatus purged with argon. After the temperature of the solution had been raised to 60° C., sodium hydride (1.3 g, 0.054 mole) freshly washed with dried benzene was added in portions and then the mixture was held at this temperature for 1 h. Allyl bromide (10 ml, 0.116 mole) was added dropwise to the stirred reaction mix and the temperature increased to 110° C. during the addition. When the temperature had dropped back to 90° C. after completion of the addition the reaction mix was brought to 120° C. and kept at this temperature for 2 h. After cooling the reaction mixture was diluted with water (50 ml) and the product extracted with ether (2×50 ml). The combined etherial extracts were washed with dilute brine (50 ml), dried with $NaSO_4$ and evaporated to dryness.

The crude residue was recrystallized from $CHCl_3$/MeOH and then toluene/heptane to give colourless crystals of the octa allyl ether (0.61 g, 46%) mp 226°–229° C. Found: C, 82.6; H, 9.3. $(C_{14}H_{18}O)_8$ requires C, 83.1; H, 9.0%. $^1H$ n.m.r. $(CDCl_3)$ δ: 1.11, s, $(CH_3)_3C$ ; 4.02, m, 32H, $CH_2$ and $OCH_2$; 4.84, m, 4.94, m, 5.12, m, 16H. $=CH_2$ 5.74, m, 8H, —CH =; 7.00, s, 16H, aromatic.

Epoxidation of the allyl ether

The allyl ether (1.616 g, 0.001 mole) in dichloromethane (10 ml) was mixed with a solution of m-chloroperbenzoic acid (1.38 g, 0.008 mole) in dichloromethane (10ml) and stirred at room temperature for 24 h. At the end of this time the precipitated m-chlorobenzoic acid was filtered off (usually less recovered than the theoretical amount) and the filtrate was passed through a short column packed with neutral alumina in order to remove the rest of the acid and peroxides. Fractions were collected, checked for absence of peroxides and evaporated. A total of 1.090 g of material was recovered from the column in two main fractions. $^1H$ nmr. indicated the presence of epoxy groups in both fractions. This resin had an epoxy equivalent weight of 499 g.

Example—Preparation of the epoxy resin from C-Methylcalix[4]resorcinarene

Method A

C-Methylcalix14]resorcinarene (50 g, 0.0919 mole) which was prepared by the method of Cram et al, 1988, J. Am. Chem. Soc, 110, 2229 was added to a mixture of epichlorohydrin (340 g, 288 ml, 3.7 mole), 2-propanol (288 ml) and methanol (96 ml) and stirred. After a short time a solution was obtained and the temperature was raised to 50° C. in an oil bath. To this solution was added dropwise a solution of NaOH (29.4 g, 0.735 mole) in methanol (2130 ml). The addition took about 1 h and the temperature was kept at 50° C. The reaction mixture was stirred for a further 4 h at 50° C. after the addition. On cooling, the inorganic salts were filtered off and then the filtrate was evaporated leaving a residue which was then redissolved in dichloromethane (100 ml). Insoluble matter was filtered off and the filtrate was treated with dilute brine (100 ml) and the pH adjusted to 5 with a little acetic acid. The emulsion so formed was broken by filtration through celite. After a further wash with water, the organic layer was dried over sodium sulphate and filtered. Coloured impurities were removed by passing this solution through a short (42×75 mm) column of neutral alumina. The eluate was evaporated to give the resin as a brown friable powder,(82 g), m.p.148°–154° C. $^1H$ n.m.r. $(CDCl_3)$ δ: 1.48, m; 2.74, m; 3.30, m; 3.6, sharp peaks; 3.87, m; 4.61, m; 6.33, m; 7.20, m. The n.m.r. exhibits great complexity indicating a whole family of partially epoxidized materials. This resin had an epoxy equivalent weight of 175 g which agrees with the $^1H$ n.m.r. integral data in suggesting an average of 4 epoxy groups per molecule.

Method B

C-Methylcalix[4]resorcinarene (75 g, 0.138 mole) was prepared as described in Method A above was weighed into a reaction flask and then epichlorohydrin (216 ml, 2.76 mole), 2-propanol (45 ml), methanol (21 ml) and finally N,N-dimethylbenzylamine (0.375 ml) were added, blanketed with argon and stirred mechanically. A solution was obtained quickly and the temperature was raised to 50° C. in an oil bath and maintained at this temperature with stirring for 1 h. Then a solution of NaOH (44.2 g, 1.104 mole) in water (270 ml) was added dropwise over about 1 h whilst the temperature was kept near 50° C. Stirring was continued for a further 3 h at 50° C. and then overnight at room temperature.

Next day the pH of the mixture was adjusted to approximately 5 by the addition of glacial acetic acid in about 50% of the runs done, two phases separated in the reaction flask allowing easy separation of the upper aqueous phase and simplification of the subsequent evaporation). The organic phase was then evaporated to dryness. If on the other hand two phases failed to separate the whole reaction mixture was evaporated to dryness. The solid residue was extracted with dichloromethane (400 ml) by mechanical stirring (the epoxy resin is very soluble in dichloromethane) and was filtered off on a large Buchner funnel having a layer of celite to aid the rather difficult filtration. The residue was re-extracted with further dichloromethane (200 ml) and the combined dichloromethane extracts were washed once with water (200 ml), dried with $Na_2SO_4$ and evaporated to dryness. The residue is once again dissolved in dichloromethane (300 ml) and filtered once again through celite to obtain a clear solution. Evaporation to dryness yielded the epoxy resin as a friable light buff powder (84.7 g) of epoxy equivalent weight 195 g and mp 172°–192° C.

Example 2—Preparation of epoxy resin from C-ethylcalix[4]resorcinarene

C-Ethylcalix[4]resorcinarene prepared by the established procedure was treated with epichlorohydrin as described in Example 1 above to give a resin as a friable solid with an epoxy equivalent weight of 238 g.

Example 3—Epoxy resin from C-isopropylcalix[4]resorcinarene

The starting C-isopropylcalix[4]resorcinarene prepared by a variation of the established procedure was treated as in Example 1 above with epichlorohydrin to give a resin softening at 120°–125° C. and with an epoxy equivalent weight of 247 g. $^1H$ n.m.r. $(CDCl_3)$ was complex: 0.85, m, 20–24H; 1.5, m, 4H; 2.73, m. approx. 12H; complex region 3-4.6; 6.35,m, approx. 3H; 7.2, m, approx 2H.

Example 4—Epoxy resin from C-phenylcalix-[4]resorcinarene

Resorcinol (80.2 g, 0.29 mole) and benzaldehyde (74 ml, 0.729 mole) in a mixture of 95% ethanol (580 ml) and concentrated HCl (146 ml) was stirred mechanically at 80° C. for 11 days under argon. At the end of this time the yellow precipitate was filtered and washed by suspending in 95% ethanol stirring for 30 min and then filtering; this washing procedure was repeated twice. The crude product was dissolved in 2M NaOH, filtered and then acidified with acetic acid whereupon a precipitate formed. Filtration and drying yielded the product as a brown solid, 134 g (93%). $^1$H n.m.r. (NaOD) δ: 5.62, m, 4H; 5.98, s, 4H, CH; 6.26, m, 4H; 7.14, m, 20–24H.

Preparation of the epoxy resin followed essentially the same procedure as above except that the calixarene was suspended in the reaction mixture of epichlorohydrin and alcohol. The starting material went into solution as the reaction proceeded. On work up and chromatography on alumina the resin was obtained as a dark friable solid, of epoxy equivalent weight, 186 g.

Example 5—Epoxy resins from partially methylated C-methylcalix[4]resorcinarene C-Methylcalix[4]resorcinarene (10 g, 0.018 mole) in a mixture of anhydrous $K_2CO_3$ (10.2 g) and dry acetone (200 ml) was treated with iodomethane (15.7 g. 0.11 mole) and stirred under argon at reflux for 16 h. After [filtering off the sails, the acetone solution was evaporated to dryness and partitioned between dichloromethane and dilute brine at pH 3. Further extractions with fresh dichloromethane were carried out and the combined dichloromethane layers, were washed once with brine, dried ($Na_2SO_4$) and evaporated to dryness (10.6 g). This residue was redissolved in dichloromethane, passed through a short column of Florisil (Registered Trade Mark) and the eluate evaporated to give the mixed methyl ethers, 8.1 g as an oil. HPLC showed this product to be a mixture of components but $^1$H nmr. was consistent with methylation. There was always present in these mixtures some of the octamethyl ether of C-methylcalix[4]resorcinarene, an authentic sample of which had been prepared and characterized fully.

Products of varying methoxy content were obtained by varying the amount of iodomethane used. The preparation of epoxy resins from these oils followed the procedures described above. By this means epoxy resins having epoxy equivalent weights of 241, 313, 335 and 403 g were prepared.

Example 6 Epoxy resin from C-propyl-calix[4]resorcinarene

Epoxy, resin from C-propylcalix[4]resorcinarene was made as for example 1 using the appropriate starting calixarene. The resin had m.p. 115°–130 ° C. and an epoxy equivalent weight of 215 g.

Example 7—Epoxy resin of C-methyl-2-methylcalix[4]resorcinarene

Epoxidation of the C-methyl-2-methylcalix[4]resorcinarene by the procedures already described gave an epoxy resin of epoxy equivalent weight, 221 g.

Example 8—Epoxy resin of mixed isomers-of C-methylcalix[4]resorcinarene (a) Starting calixarene A stirred mixture of resorcinol (11.01 g, 0.1 mole) and acetaldehyde (4.41 g, 0.1 mole) in water (40 ml) was acidified by careful addition of concentrated HCl (10 ml). There was an exothermic reaction and a precipitate formed rapidly. Stirring was continued for 1 h at 75° C. and then the mixture was cooled and the precipitated calixarene filtered off, washed with water and dried, (14 g). This product contains about 25% (h.p.l.c.) of the cis,trans,cis isomer and 75% of the "normal" all cis isomer described above.

(b) Epoxidation. Using the procedure above yielded an epoxy resin of the mixed isomers having m.p.118°–128° C. and an epoxy equivalent weight of 180 g.

Example 9

(a) Preparation of a typical curable formulation

The resin prepared in Example 1 (3.63 g) was added in portions with stirring to Epikote 8283 IQ (Registered Trade Mark) a commercial DGEBA type epoxy resin (4.01 g) at 127° C. The amine hardener, p-aminophenyl sulphone (DDS) (2.36 g) was added in portions to the resulting oil with stirring. Additives, for example CTBN rubbers to make toughened formulations if desired were added at this stage. This mixture was then degassed by evacuation (1 mm Hg) for 8 min and BF$_3$-ethylamine catalyst (Anchor 1948 (Registered Trade Mark)) was added in one lot with stirring. The mixture was degassed for a further 4 min under the same conditions as before.

(b) Curing and properties of a typical formulated resin

After pouring into appropriate moulds curing was accomplished by heating at 100° C. for 1 h, 140° C. for 1 h, and then 180° C. for 4 h. This neat cured resin had a $T_g$ (Tan δ max) of 281° C. and a modulus of 2.1 GPa. Neat resin fracture toughness as measured by the compact tension test was 0.40 MPa.m$^{\frac{1}{2}}$. The properties of other formulations of the resin of Example 1 are given in Table 2.

Example 10—Other Curable Formulations

The method of Example 9(a) was used to formulate resins prepared as in Examples 1–8. These formulated resins when cured as in Example 9(b) give the fracture toughness values shown in Table 2.

Example 11—Preparation of a typical prepreg

Method (a). The resin formulation (55 g) prepared as described in Example 9 (a) was dissolved in purified methyl ethyl ketone (55ml) and painted onto Fiberite (Registered Trade Mark) High Performance Structural W322 woven carbon fibre cloth. The prepreg was dried in a stream of warm air for 2 h and then "B" staged in an oven at 90° C. for 100 sec. This prepreg had a mean resin content of 43% and had good drape and slight tack. The temperature and time of "staging" was varied to suit the requirements of each formulation.

Method (b). With some formulations it was more advantageous to dissolve epoxy resin, hardener and any additives in dichloromethane, and produce the prepreg from this solution.

These prepregging solutions were also suited to machine prepregging of cloth or uni-directional tape.

Example 12—Fabrication into sample composite laminates

A 20 ply laminate was laid up from pre-preg made as in Example 9 according to BSS 7273 and cured in an autoclave under a pressure of 620 kPa using the curing schedule described above. The cured laminate had a density of 1.56 g/cm$^3$, a fibre volume of 57% and a fibre weight on weight of composite of 62.8%.

2 ply, 12 ply, and 5 ply laminates were also made from the prepreg as described above and cured in an autoclave or on a hot platten press.

Example 13—Impact characteristics

2 Ply laminates when tested on an ICI Impact tester had an average load at break of 166.1 Newtons and average energy at break of 355 Joules.

Example 14—Mode I Fracture Toughness of typical Laminates

20 Ply cloth composite laminates were prepared from pre-pregs and tested according to BSS 7273. Values for some formulations are shown in Table 4.

Example 15—Laminate Static Tensile Properties

12 Ply laminates of prepregs made from various formulations of the new resins were prepared and tested according to BMS 8-256F for Tensile properties. Results are shown in Table 5.

Example 16—Toughening of Resins with Rubbers

Admixture of CTBN rubber (Hycar 1300x13 (Registered Trade Mark), 10 p.h.r.) to a curable formulation prepared as in Example 9(a) above, followed by curing as a neat resin sample as in Example 9(b) or prepregging the formulation and then preparation of a laminate as in Examples 11 and 12. yielded samples that were significantly tougher than untreated samples (Tables 2 and 6).

TABLE 2
Properties of Cured Formulated Resins

| Resin | Tg | Mode of toughening | Additive % | Fracture Toughness Kq* |
|---|---|---|---|---|
| Example 1 | 281 | none | none | 0.40 |
| Example 1 | 282 | CTBN 1300 × 8 | 5 | 0.46 |
| Example 1 | 284 | CTBN 1300 × 8 | 10 | 0.57 |
| Example 1 | 277 | CTBN 1300 × 8 | 15 | 0.51 |
| Example 1 | 290, 235 | CTBN 1300 × 8 | 20 | 0.53 |
| Example 1 | 285 | CTBN 1300 × 13 | 10 | 0.68 |
| Example 1 | 288 | CTBN 1300 × 13 | 15 | 0.58 |
| Example 1 | 293 | ULTEM | 10 | 0.65 |
| Example 2 | 277 | none | none | 0.56 |
| Example 3 | 271 (225) | none | none | 0.44 |
| Example 4 | | none | none | 0.49 |
| Example 5 (EQW 313) | 210 | Methylation | none | 0.81 |
| Example 5 (EQW 241) | 216 | Methylation | none | 0.53 |
| Example 6 | | none | none | 0.44 |
| Example 7 | 282 (212) | none | none | 0.50 |
| Example 8 | | none | none | 0.57 |
| Resin A | 199 | none | none | 0.52 |

Notes:
All resins were cured under the a same conditions with $BF_3$-ethylamine catalyst present (0.33 phr).
*Fracture toughness based on multiple values, in the units $Mpa.m^{\frac{1}{2}}$

TABLE 3
Comparison of Tg values (DMTA) obtained for some of the cured neat calixarene epoxy resin formulations and some other glycidyl ether resin formulations

| Resin System | Tg (Tan δ) °C. | Description |
|---|---|---|
| DGEBA | 211 | |
| Xanthene[1] | 242 | |
| Example 1 | 281 | |
| Example 2 | 277 | |
| Example 3 | 271 (225) | D[2] |
| Example 5 (EQW[3] 313) | 210 | |
| Example 7 | 282 (212) | D[2] |
| Resin A | 199 | B[4] |

Notes:
[1] Experimental resin of Diglycidyl ether type
[2] Shoulder on lower temperature side of Tan δ curve
[3] Epoxy Equivalent weight
[4] Broad Tan δ peak

TABLE 4
Mode I Fracture Toughness Values for some Typical Laminates

| Formulation | Fracture Toughness $J/m^2$ | | |
|---|---|---|---|
| | Initiation | arrest | area |
| 1 (Resin Example 1) | 370 | 232 | 288 |
| 2 (Resin Example 2 | 321 | 237 | 267 |
| 3 (Resin Example 1) | 327 | 197 | 257 |
| 5 (Resin Example 6) | 380 | 246 | 305 |

TABLE 5
Some Static Tensile properties of Typical Laminates

| Formulation | Ultimate Tensile Strength MPa | Modulus of Elasticity (GPa) | Ultimate Tensile Strain (%) |
|---|---|---|---|
| 1 (Resin Example 1 | 585 | 61.2 | 0.957 |
| 2 (Resin Example 2) | 561 | 58.2 | 0.965 |
| 4 (Resin Example 1) | 596 | 58.7 | 1.017 |

TABLE 6
Effect of added CTBN Rubber on the Mode I Fracture Toughness Values of Laminates containing Resin from Example 1

| Formulation | Fracture Toughness $J/m^2$ | | |
|---|---|---|---|
| | Initiation | arrest | area |
| 1 (Resin Example 1) no rubber | 370 | 232 | 288 |
| 4 (Resin Example 1), 10 p.h.r. of CTBN rubber | 477 | 279 | 364 |

We claim:

1. A macrocyclic compound of the formula (I)

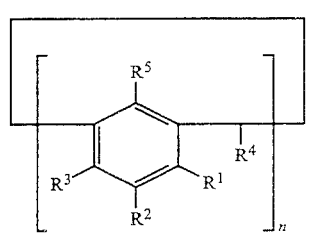

wherein
n is an integer from 3 to 10;
$R^1$ and $R^3$ are either the same or different and are hydrogen, hydroxyl, alkoxy, allyloxy, or epoxypropyloxy;

$R^2$ is hydrogen, aralkyl optionally substituted with halogen, alkyl optionally substituted with halogen, or aryl optionally substituted with halogen;

$R^4$ is hydrogen, alkyl optionally substituted with halogen, aralkyl optionally substituted with halogen, or aryl optionally substituted with alkyl and/or halogen;

$R^5$ is hydrogen, aryl or alkyl;

with the proviso that the compound contains on average at least one epoxy group per molecule.

2. A compound as claimed in claim 1, characterized in that each of $R^1$ and $R^3$ is hydroxyl, alkoxy or epoxypropyloxy, $R^2$ is hydrogen, $R^4$ is methyl, ethyl or propyl and $R^5$ is hydrogen.

3. A compound as claimed in claim 2, characterized in that the number of hydroxyl (or hydroxyl+alkoxy) groups present is approximately equal to the number of epoxypropyloxy groups.

4. A method for the preparation of a macrocyclic compound of the formula (I) as claimed in claim 1, characterized in that said method comprises epoxidizing a compound of the formula

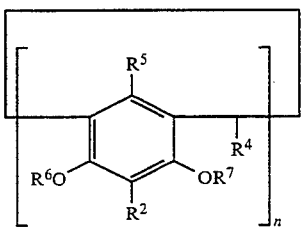

(II)

wherein n, $R^2$, $R^5$ and $R^4$ are as defined for the compound of formula (I) in claim 1 and $R^6$ and $R^7$ are either the same or different and are selected from hydrogen or a masking group, with the proviso that at least one of $R^6$ and $R^7$ is hydrogen.

5. A method as claimed in claim 4, characterized in that the epoxidation is performed using epichlorohydrin.

6. A curable epoxy resin formulation, characterized in that the resin formulation comprises at least macrocyclic compound of the formula (I) as defined in claim 1, together with other epoxy resins and/or additives selected from the group consisting of toughening polymers, hardeners, reinforcements, fillers and catalysts.

7. A curable epoxy resin formulation as claimed in claim 6, characterized in that the other epoxy resin is a diglycidyl ether of bisphenol A (DGEBA) and the additive is 4,4'-diaminodiphenylsulphone or $BF_3$-ethylamine.

8. An impregnated fibre reinforced material, characterized in that the fibre reinforcements are impregnated with an epoxy resin formulation as claimed in claim 6.

9. An advanced composite material comprising a fibrous material in a matrix of a cured epoxy resin, characterized in that the cured epoxy resin is formed from an epoxy resin formulation as claimed in claim 6.

10. A method as claimed in claim 4 wherein the masking group is an alkyl group.

* * * * *